United States Patent
Hofmann et al.

(10) Patent No.: US 8,232,061 B2
(45) Date of Patent: Jul. 31, 2012

(54) METHOD AND DEVICE FOR EXAMINING THE ATTACHMENT OR DETACHMENT OF LIVING OR DEAD CELLS OR CELL-LIKE PARTICLES OR OTHER SURFACE ACCUMULATIONS ON SURFACES BY MEANS OF PLASMON RESONANCE AND USE OF SAID METHOD AND SAID DEVICE

(75) Inventors: Andreas Hofmann, Wallenfels (DE); Norbert Danz, Jena (DE); Silke Hofmann, Wallenfels (DE); Michael Keusgen, Marburg/Lahn (DE); Ulla Magdolen, Kirchheim (DE)

(73) Assignee: Andreas Hofmann, Wallenfels (DE)

( * ) Notice: Subject to any disclaimer, the term of this patent is extended or adjusted under 35 U.S.C. 154(b) by 489 days.

(21) Appl. No.: 12/525,418

(22) PCT Filed: Feb. 1, 2008

(86) PCT No.: PCT/EP2008/000826
§ 371 (c)(1),
(2), (4) Date: Jul. 31, 2009

(87) PCT Pub. No.: WO2008/092704
PCT Pub. Date: Aug. 7, 2008

(65) Prior Publication Data
US 2010/0028903 A1    Feb. 4, 2010

(30) Foreign Application Priority Data
Feb. 1, 2007  (DE) .................. 10 2007 005 147

(51) Int. Cl.
*G01N 33/53* (2006.01)

(52) U.S. Cl. ....................................... 435/7.2

(58) Field of Classification Search .................. None
See application file for complete search history.

(56) References Cited

U.S. PATENT DOCUMENTS

| | | | | |
|---|---|---|---|---|
| 5,917,607 A | * | 6/1999 | Naya | 356/445 |
| 6,801,317 B2 | * | 10/2004 | Hofmann | 356/445 |
| 7,858,679 B2 | * | 12/2010 | Messersmith et al. | 524/17 |
| 7,973,934 B2 | * | 7/2011 | Hofmann et al. | 356/445 |

FOREIGN PATENT DOCUMENTS

| | | |
|---|---|---|
| EP | 0 286 195 | 10/1988 |
| EP | 0 305 109 | 3/1989 |
| WO | 02/39095 | 5/2002 |

OTHER PUBLICATIONS

Wolfgang Vornholt et al: "SPR Studies of Carbohydrate-Lectin . . ." Biosensors and Bioelectronics 22, 2007, pp. 2983-2988 (in English).
Saikat Datta Mazumdar et al: "Rapid Method for Detection of . . ." Biosensors and Bioelectronics 22, 2007, pp. 2040-2046 (in English).

* cited by examiner

*Primary Examiner* — Ann Lam
(74) *Attorney, Agent, or Firm* — Michael J. Striker

(57) ABSTRACT

A method for examining an attachment or detachment of living cells, dead cells or cell-like particles on a surface using plasmon resonance includes irradiating a measurement region with beams over the entire angle of incidence spectrum and capturing, combining and evaluating beams with identical angles of incidence reflected from different points of the measurement region with a determination of the angle of light incidence with a lowest reflected light intensity and measuring an angle of incidence shift of an intensity minimum that occurs. The evaluating includes registering different angles of incidence of two or more intensity minima occurring simultaneously to reflect a respective level of the surface accumulations.

7 Claims, 2 Drawing Sheets

METHOD AND DEVICE FOR EXAMINING THE ATTACHMENT OR DETACHMENT OF LIVING OR DEAD CELLS OR CELL-LIKE PARTICLES OR OTHER SURFACE ACCUMULATIONS ON SURFACES BY MEANS OF PLASMON RESONANCE AND USE OF SAID METHOD AND SAID DEVICE

The invention relates to a method and a device for examining the attachment or detachment of living or dead cells or cell-like particles or other surface accumulations on surfaces by means of plasmon resonance and also to the use of said method and said device.

The phenomenon of surface plasmon resonance (SPR) involves a collective excitation of the electrons at the surface of a layer having free electrons. The resonant frequency of the surface plasmons is highly sensitive to the refractive index of the medium adjoining the sensitive surface. This is utilized to measure thin layers with regard to the refractive index or the layer thickness.

In biosensor technology, in particular, this effect is utilized to examine the attachment kinetics of biomolecules from a sample liquid to a functionalized metal surface. For this purpose, the resonance condition of the surface plasmons is detected in a temporally resolved manner. The surface plasmons of the thin metal layer are excited by light that falls onto the metal layer at a specific angle or within an angle range. The resonance condition is then met for a specific combination of wavelength and angle of incidence. Under this resonance condition, the intensity of the light reflected at the metal layer is significantly reduced on account of the generation of the surface plasmons. In order to find the resonance condition, either the angle of incidence (given a constant wavelength) or the wavelength (given a constant angle of incidence) can be tuned and the intensity of the reflected light can be detected. In general, a gold-coated glass body (prism) and light of constant wavelength are employed, said light impinging on the gold layer with an angle of incidence spectrum appropriate for the plasmon resonance.

WO 02/39095 discloses a plasmon resonance sensor in which light with an angle of incidence spectrum appropriate for the plasmon resonance is directed onto a measurement region at the reflective inner side of a metal layer or semiconductor layer applied to a light-transmissive body, said layer bearing on the outer side of the surface that is brought into contact with the sample liquid containing the biomolecules or the cells, wherein the individual measurement points of the measurement region are irradiated with the entire angle spectrum and the beams which have identical angles of incidence in each case and are reflected from different points of the measurement region are combined and captured and evaluated continuously during a time period with the determination of the angle of light incidence with the reflected lowest light intensity and the angle of incidence shift of the intensity minimum that occurs is measured in the process.

In this case, not just the state at one point of the measurement area is considered and evaluated, as is the case for example from EP 305 109 B1 with the focusing of a beam fan onto one point of the measurement area; rather, an areal light source in the form of an optical waveguide having a thick core diameter is used for the divergent irradiation of the measurement region points in each case with the entire angle spectrum, wherein a plurality of parallel measurements are carried out simultaneously with the irradiated measurement region subdivided into narrow adjacent measurement channels. The simultaneous detection of the entire measurement area region by means of the combination—effected with a collimation lens—of the reflected beams having identical angles of incidence serves for obtaining average values of the signals obtained and is intended to prevent measured value corruptions by local inhomogeneities of the metal layer or of the surface.

Here, too, as in all other known plasmon resonance sensors, a uniform attachment on the surface is assumed and accordingly a single minimum is assumed, which shifts relative to the angle of incidence with increasing attachment (layer thickness). It has surprisingly been ascertained, however, that upon the attachment of cells to a correspondingly sensitized or functionalized surface, not only does a shift of the minimum arise; rather, in the case of measurements with cells, during the measurements taking place over several hours or even days, a splitting of the measured signal into at least two minima which occur simultaneously can occur, said minima being assigned to different angles of incidence.

The invention is based on this ascertainment, the invention being characterized in that the evaluation of the reflected light is carried out in such a way that even two or more intensity minima that occur simultaneously within the time period, for different angles of incidence, are registered in a time-dependent manner, wherein the registered measurement signals reflect the respective level of the surface accumulations.

The method according to the invention thus for the first time affords the possibility of tracking cell attachment processes in a continuous method n a temporally unrestricted manner and also quantitively with the exclusion of the subjective impression of the observer, and of drawing conclusions about the binding behavior of cells. To date it has been possible to obtain statements about cell adhesion only by means of visual methods for example by using a microscope or a spectrophotometer, but this permits only a direct observation and does not permit automated evaluation of the attachment process. It is only by means of this automated evaluation that special characteristics that possibly occur only for a short time can also be reliably detected and documented during a long examination process that proceeds continuously for several days, if appropriate. In this case, the previous examination methods mentioned above can be used in addition to the method according to the invention in a targeted manner in order to be able to correctly interpret the occurrence of the minima.

According to the inventors, insights, for example the occurrence of a double minimum or the resolution thereof following a specific time can indicate the beginning or the end of a cell adhesion. Consequently, in a simple manner for different uncoated and coated synthetic and natural surfaces and for different living or dead cells it is possible to obtain statements about the respective adhesion behavior and about the associated temporal conditions, which affords advantages in many different regards.

The invention promises great benefits in a wealth of different fields, namely

- in the field of biology or medicine for measuring cell surface interaction, e.g. inflammation cells, cells involved in wound healing, cells involved in embryo development, cells involved in tissue restructuring and cells involved in a malignant situation;
- in foodstuff technology e.g. for measuring the influence of substances that are taken up by the food and metabolized on the body cells in the living organism, e.g. binding of germs to body cells;
- in bacteriology for examining the virulence of fungi, bacteria, viruses, single cell organisms (amoebas), and parasites (worms);

measurement for synthetic cells such as liposomes which are used for transporting pharmaceuticals and therapeutic DNA;

binding of non-biological compact particles to cells e.g. when measuring the interaction of abraded material from implants with endogenous cells or the particles of contrast medium with endogenous cells (magnetofection);

measuring the binding of stones and crystalline structures of cells, e.g. kidney stones or gallstones.

The method according to the invention thus serves for checking the effectiveness of substances that promote or decrease cell adherence (pharmacodynamics) or else the behavior of biological or non-biological substances in the physiologically or pathophysiologically altered organisms.

The invention also relates to a device with a plasmon resonance sensor comprising a light-transmissive body, a reflective metal layer or semiconductor layer applied to an area of the body and having a surface that can be sensitized for cell attachments, a light source for generating a beam path that is incident on a measurement region of the inner side of the layer through the body with an angle spectrum that falls onto all points of the measurement region comprising a converging optical unit for combining emerging beams having identical angles of incidence, and comprising a detector which captures the reflected emerging beam path and ascertains in a time-dependent manner the angle of incidence of the light that changes as a result of attachments to the sensitive surface, in the case of which an intensity minimum of emerging light occurs in a manner governed by resonance, wherein the detector is assigned an evaluation unit with software for the time- and angle-dependent continuous registration of the intensity minimum. Such a device is likewise known from WO 02/39095.

According to the invention, in this device, the evaluation unit and the software are constituted such that they ascertain and register in a time-dependent manner even two or more intensity minima that occur at the same time.

In the device according to the invention, too, the measurement region is advantageously subdivided into two or more narrow parallel measurement channels that are assigned separate detector regions each with dedicated signal registration.

Finally, the invention also relates to the use of the method and of the device for examining the attachment or detachment of cells or cell-like particles in the field of biology/medicine for measuring cell surface interaction, in the field of foodstuff technology for measuring the behavior of nutrient substances and germs with respect to body cells, in bacteriology for examining the virulence of fungi, bacteria, viruses, single cell organisms or parasites, for measuring the binding behavior of synthetic cells such as liposomes to body cells, for measuring the binding of non-biological particles to endogenous cells or for examining the binding of stones or crystalline structures of cells to endogenous cells. Supplementary explanations concerning these application possibilities can be found in the explanations above.

The invention is explained below on the basis of an exemplary embodiment of the device.

Figure 1:
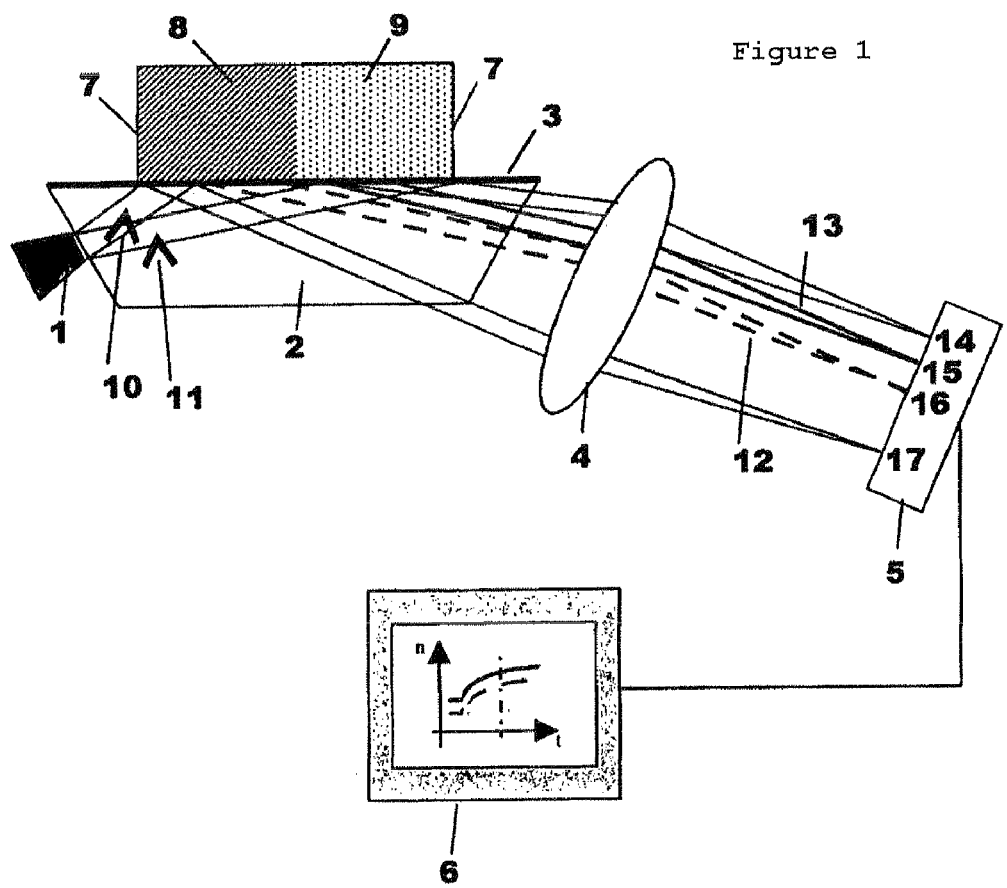
FIG. 1 shows in a schematic illustration a plasmon resonance sensor according to the invention.

In FIG. 1, an extended monochromatic light source 1 is provided, which is assigned to a glass prism 2 bearing a gold layer 3 on its top side. A collimation lens 4 is arranged in the beam path that emerges from the light source 1 and is reflected by the gold layer 3, said collimation lens directing the beams onto a detector 5, to which an evaluation unit 6 is connected.

The gold layer 3 has on its top side a measurement region delimited by interfaces 7, the sample liquid (solution) with the cells being in contact with said measurement region. For illustration purposes, said sample liquid is subdivided into a medium 8 (refractive index $n_1$) and a medium 9 (refractive index $n_2$). This division into two corresponds to the conception of two different cell states during an attachment process which results in simultaneously occurring minima of the SPR signal at different positions.

The limiting beams emerging from the edges of the extended light source 1 are depicted, which represent an incident beam bundle 10 having a minimum angle of incidence and a beam bundle 11 having a maximum angle of incidence and thus exhibit the irradiation at different points of the gold layer 3 with identical angles of incidence. In this case, FIG. 1 illustrates how the collimation optical unit 4 combines the beams having identical angles of incidence on the detector 5 at the converging points 14 and 17, respectively.

From the emerging beam path, intervening light beams 12 each having identical angles of incidence and light beams 13 having a different, likewise uniform angle of incidence are additionally depicted, which are combined at the detector 5 at the points 16 and 15, respectively. The angles of incidence involved here are those which are to be assigned to the different media 8 and 9 or to the two refractive indices $n_1$ and $n_2$, in the case of which an intensive attenuation of the beam intensity occurs in a manner governed by resonance. The points 15 and 16 and hence the assigned angles of incidence shift in a time-dependent manner during the attachment process between the points 14 and 17.

The evaluation unit 6 equipped with corresponding software detects the minima ascertained by the detector 5, a CCD camera, and registers them continuously during the entire period of the experiment. As indicated, the evaluation unit 6 comprises an optical display (screen), on which the profile of the two minima can be displayed. This is done in a diagram with the refractive index n plotted against the time axis t.

Figure 2:
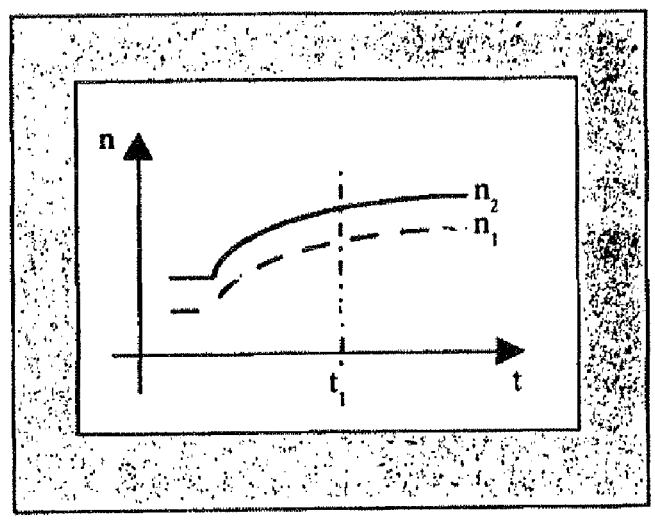
FIG. 2 shows the diagram indicated in FIG. 1 in an enlarged illustration.

FIG. 2 shows the refractive index diagram from FIG. 1 in an enlarged illustration. The diagram contains two completely separate curves for $n_1$ and $n_2$, that is to say two minima during the entire examination duration registered.

In a departure from this however—with the use of a different sample liquid with different cells and with differently prepared surfaces—the minimum values $n_1$ and $n_2$ can also coincide occasionally, which corresponds with the detection of just a single intensity minimum, or appear simultaneously for a limited period or diverge after a certain time period and, if appropriate, merge together again after a further time period.

Figure 3:
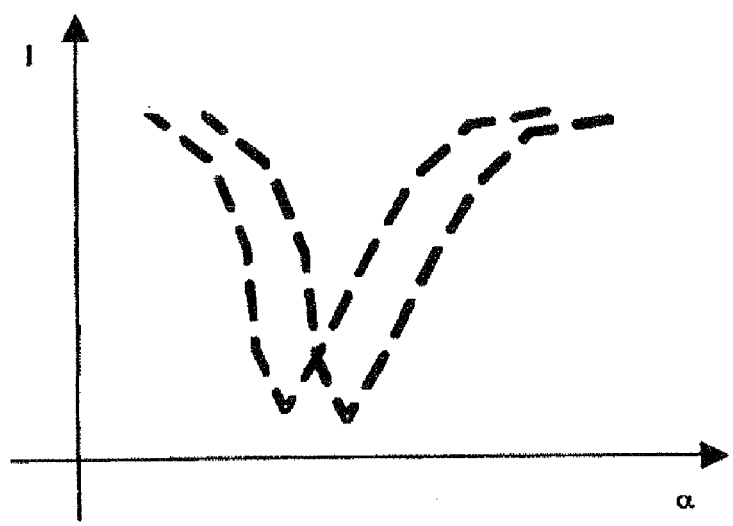
FIG. 3 shows, for the instant $t_1$ (FIG. 2) the intensity of the emerging light for different angles of incidence.

FIG. 3 represents a snapshot at the instant $t_1$ in FIG. 2 which was likewise detected and can be displayed by the evaluation unit 6 and in which the light intensity I of the reflected light is represented against the angles of incidence $\alpha$ of the light (measured in pixels corresponding to the angles of incidence). In accordance with the double minima $n_1$ and $n_2$ in FIG. 2, two curves arise each respectively having a minimum that is respectively assigned to a very specific angle of incidence.

Figure 4:
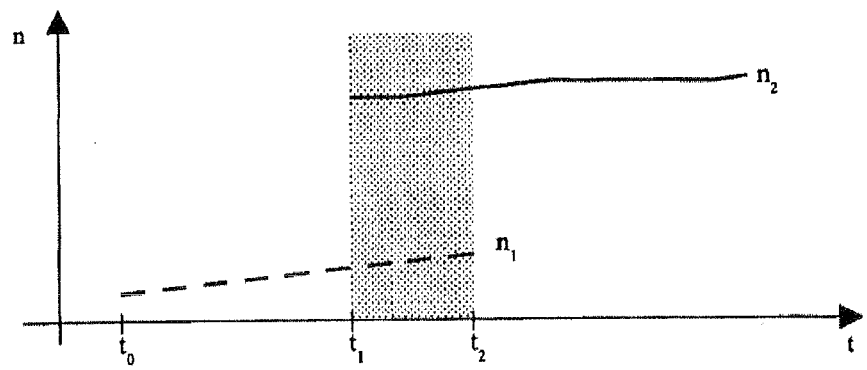
FIG. 4 shows an experimental result evaluated in accordance with the illustration in FIG. 2 for an adhesion of osteoplasts.

FIG. 4 with a diagram corresponding to FIG. 2 is based on the following experimental procedure: the cleaned gold layer 3 in accordance with FIG. 1 was coated with fibronectin, an extracellular glycoprotein, in a concentration of 1 mg/ml in the region of a first measurement channel. As a negative control, a second parallel measurement channel on the gold layer 3 was coated with calf serum albumin in a concentration of 1 mg/ml. After this preparation, osteoplasts (living endothelial cells) were added into both measurement channels in a concentration of 225 000 to 300 000/ml. This solution (buffer solution) was circulated through the measurement channels, such that continuous intermixing took place and loose deposits on the surface were washed away. For the first measurement channel it was thereupon possible to ascertain a temporally shifting refractive index n as a consequence of an intensity minimum of reflected light, which is plotted against time t in FIG. 4.

The refractive index signal commencing at the instant $t_0$ is represented as measurement curve $n_1$ in FIG. 4. After about 20 minutes ($t_1$), the sudden occurrence of a second refractive index, which is depicted as measurement curve $n_2$ in FIG. 4, was ascertained, corresponding to the simultaneous occurrence of two intensity minima. This state was maintained for approximately 12 minutes until the instant $t_2$, whereupon suddenly a signal was no longer registered for $n_1$ and only the temporally continuing signal for $n_2$ arose.

In the second measurement channel for the negative control, by contrast, it was not possible to ascertain two simultaneous minima as in the time window $t_1$ to $t_2$ highlighted in FIG. 4. The occurrence of the double minimum in the time window $t_1$ to $t_2$ must therefore be regarded as typical of adhesion and can be assigned temporally to the adhesion process that takes place only in the measurement channel 1.

The invention claimed is:

1. A method for examining an attachment or detachment of living cells, dead cells, cell-like particles or other surface accumulations on a surface using plasmon resonance, in which light with an angle of incidence spectrum appropriate for the plasmon resonance is directed onto a measurement region at the reflective inner side of a metal layer or semiconductor layer applied to a light-transmissive body, said layer bearing on the outer side of the surface that is brought into contact with the sample liquid containing the cells, comprising the steps of:
   irradiating individual measurement points of the measurement region with beams over the entire angle of incidence spectrum;
   continuously capturing, combining and evaluating the beams which have identical angles of incidence and are reflected from different points of the measurement region during a time period with a determination of the angle of light incidence with a lowest reflected light intensity and measuring an angle of incidence shift of an intensity minimum that occurs; and
   wherein the evaluating of light comprising the reflected beams includes registering different angles of incidence of two or more intensity minima that occur simultaneously within the time period, said registering reflecting a respective level of the surface accumulations.

2. The method as claimed in claim 1, wherein an areal light source is used for irradiating the measurement region points in each case with the entire angle of incidence spectrum.

3. The method as claimed in claim 1, wherein two or more parallel measurements are carried out simultaneously with the irradiated measurement region subdivided into narrow adjacent measurement channels.

4. The method as claimed in claim 1 for application in any of the group consisting of: the field of biology/medicine for measuring cell surface interaction, the field of-foodstuff technology for measuring the behavior of nutrient substances and germs with respect to body cells, and the field of bacteriology for examining the virulence of fungi, bacteria, viruses, single cell organisms or parasites, for measuring the binding behavior of synthetic cells and measuring the binding of non-biological particles to endogenous cells or for examining the binding of stones or crystalline structures of cells to endogenous cells.

5. The method as claimed in claim 4, wherein the measuring of binding behavior of synthetic cells in the field of bacteriology comprises measuring the binding behavior of liposomes to body cells.

6. A device for examining an attachment or detachment of living cells, dead cells, cell-like particles or surface accumulations using plasmon resonance, comprising:
   a light-transmissive body (2),
   a reflective metal layer (3) or semiconductor layer applied to an area of the body (2) and having a surface that can be sensitized for cell attachments,
   a light source (1) for generating a beam path (10, 11) that is incident on a measurement region of the inner side of the layer (3) through the body (2) with an angle spectrum that falls onto all points of the measurement region,
   a converging optical unit (4) for combining reflected emerging beams (12; 13) having identical angles of incidence,
   a detector (5) which captures a path of the reflected emerging beam path (12, 13) and ascertains, in a time-dependent manner, the angle of incidence that changes as a result of attachments to the sensitive surface, in the case of which an intensity minimum of emerging light occurs in a manner governed by resonance, and
   an an evaluation unit (6) with software for the time- and angle-dependent continuous registration of the intensity minimum,
   wherein the evaluation unit (6) and the software are programmed to ascertain and register, in a time-dependent manner, two or more intensity minima that occur at the same time.

7. The device as claimed in claim 6, wherein the measurement region is subdivided into two or more narrow parallel measurement channels that are assigned separate detector regions each with dedicated signal registration.

* * * * *